United States Patent [19]
Calverley et al.

[11] Patent Number: 5,710,142
[45] Date of Patent: Jan. 20, 1998

[54] VITAMIN D ANALOGUES

[75] Inventors: Martin John Calverley, Herlev; Henrik Pedersen, Bagsværd, both of Denmark

[73] Assignee: Leo Pharmaceutical Products Ltd. A/S (Løvens Kemiske Fabrik Produktionsaktieselskab), Ballerup, Denmark

[21] Appl. No.: 428,187

[22] PCT Filed: Nov. 1, 1993

[86] PCT No.: PCT/DK93/00351

§ 371 Date: May 2, 1995

§ 102(e) Date: May 2, 1995

[87] PCT Pub. No.: WO94/10139

PCT Pub. Date: May 11, 1994

[30] Foreign Application Priority Data

Nov. 4, 1992 [GB] United Kingdom ............ 9223061

[51] Int. Cl.$^6$ .................... A61K 31/59; C07C 401/00
[52] U.S. Cl. ........................................ 514/167; 552/653
[58] Field of Search ........................ 552/653; 514/167

[56] References Cited

U.S. PATENT DOCUMENTS

| | | | |
|---|---|---|---|
| 4,594,432 | 6/1986 | Baggiolini et al. | 549/214 |
| 4,612,308 | 9/1986 | Baggiolini et al. | 514/167 |
| 4,617,297 | 10/1986 | Boris et al. | 514/167 |
| 4,711,881 | 12/1987 | Ikekawa | 514/167 |
| 4,719,205 | 1/1988 | DeLuca et al. | 514/167 |
| 4,804,502 | 2/1989 | Baggiolini et al. | 260/397.2 |
| 4,832,875 | 5/1989 | Ikekawa | 260/397.2 |
| 4,851,401 | 7/1989 | DeLuca et al. | 514/167 |
| 4,868,165 | 9/1989 | Ikekawa | 514/167 |
| 5,190,935 | 3/1993 | Binderup et al. | 514/167 |
| 5,194,431 | 3/1993 | DeLuca et al. | 514/167 |
| 5,200,536 | 4/1993 | Ikekawa et al. | 552/653 |
| 5,260,290 | 11/1993 | DeLuca et al. | 514/167 |
| 5,292,728 | 3/1994 | Neef et al. | 514/167 |

FOREIGN PATENT DOCUMENTS

| | | |
|---|---|---|
| 441467 | 8/1991 | European Pat. Off. . |
| 450743 | 10/1991 | European Pat. Off. . |
| 91 15475 | 10/1991 | WIPO . |

OTHER PUBLICATIONS

Kobayashi, et al: "Production oand specificity of anti-22-oxacalcitriol antisera", Chemical and Pharmaceutical Bulletin, vol. 40, No. 6, Jun. 1992, pp. 1520–1522, see the whole document.

Calverley: "Synthesis of MC 903, a biologically active vitamin D metabolite analogue", Tetrahedron, vol. 43, No. 20, 1987, pp. 4609–4619, see the whole document.

*Primary Examiner*—Kimberly J. Prior
*Attorney, Agent, or Firm*—Cushman Darby & Cushman IP Group Pillsbury Madison & Sutro LLP

[57] ABSTRACT

The invention relates to 20(S)-vitamin D compounds having the following formula

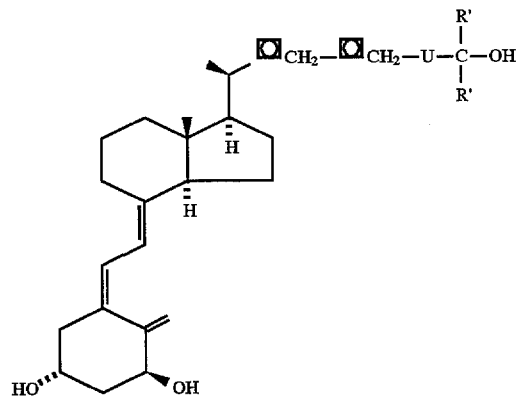

where U and R' are as defined in the specification. The compounds have strong antiinflammatory and immunomodulating activity. There are also useful in the inhibition of proliferation of undesirable cells.

7 Claims, No Drawings

VITAMIN D ANALOGUES

The application is a 371 of international application PCT/DK93/00351, filed Nov. 1, 1993.

This invention relates to a hitherto unknown class of compounds which shows antiinflammatory and immunomodulating effects as well as strong activity in inducing differentiation and inhibiting undesirable proliferation of certain cells, including cancer cells and skin cells, to pharmaceutical preparations containing these compounds, to dosage units of such preparations, and to their use in the treatment and prophylaxis of hyperparathyroidism, particularly secondary hyperparathyroidism associated with renal failure, of a number of disease states including diabetes mellitus, hypertension, ache, alopecia, skin ageing, imbalance in the immune system, of inflammatory diseases such as rheumatoid arthritis and asthma, of diseases characterized by abnormal cell differentiation and/or cell proliferation such as e.g. psoriasis and cancer, for prevention and/or treatment of steroid induced skin atrophy, and for promoting osteogenesis and treating osteoporosis.

The compounds of the present invention are derivatives of 1α,25-dihydroxy-20-epi-vitamin $D_3$ as represented by the general formula I

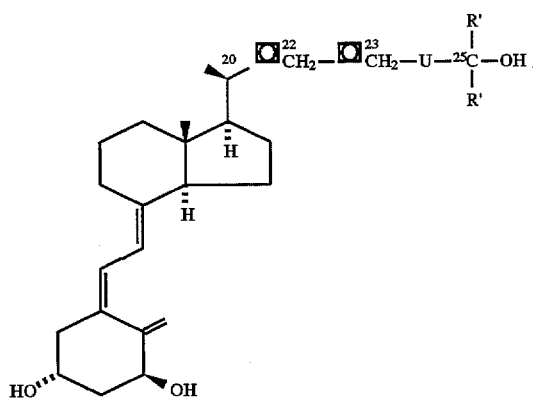

in which formula the "α" indicates that this carbon may be modified, and the moiety U, substituting the 24-methylene of 1α,25-dihydroxy-20-epi-vitamin $D_3$, stands for $(CH_2)_n$—Y—$(CH_2)_m$, where n is 0, 1 or 2, m is 1 or 2, and Y is oxygen or sulphur; and derivatives formed by replacing either the 22-methylene or the 23-methylene by an oxygen or by replacing 22- and 23-methylene with —CH=CH—; R' is methyl or ethyl; and in which one or more carbon atoms directly bonded to C-25 may optionally be substituted with one or more fluorine atoms.

Depending on the nature of the chain linking C-20 and C-25, the compounds of the invention can comprise several isomeric forms (e.g. R or S configuration at asymmetric carbon atoms, E or Z configuration of double bonds). The invention covers all these diastereoisomers in pure form or as diastereomeric mixtures. In addition, derivatives of I in which one or more of the hydroxy groups are masked as groups which can be reconverted to hydroxy groups in vivo are also within the scope of the invention.

The compounds I in which the hydroxyl group on carbon-25 is replaced by hydrogen are another type of prodrug. These compounds are relatively inactive in vitro, but are converted to active compounds of formula I by enzymatic hydroxylation after administration to the patient.

It has been shown that 1α,25-dihydroxy-vitamin $D_3$ (1,25 $(OH)_2D_3$) influences the effects and/or production of interleukins (Muller, K. et al., Immunol. Lett. 17, 361–366 (1988)), indicating the potential use of this compound in the treatment of diseases characterized by a dysfunction of the immune system, e.g. autoimmune diseases, AIDS, host versus graft reactions, and rejection of transplants or other conditions characterized by an abnormal interleukin-1 production, e.g. inflammatory diseases such as rheumatoid arthritis and asthma.

It has also been shown that 1,25$(OH)_2D_3$ is able to stimulate the differentiation of cells and inhibit excessive cell proliferation (Abe, E. et al, Proc. Natl. Acad. Sci., U.S.A. 78, 4990–4994 (1981)), and it has been suggested that this compound might be useful in the treatment of diseases characterized by abnormal cell proliferation and/or cell differentiation such as leukemia, myelofibrosis and psoriasis.

Also, the use of 1,25$(OH)_2D_3$, or its pro-drug 1α-OH-$D_3$, for the treatment of hypertension (Lind, L. et al, Acta Med. Scand. 222, 423–427 (1987)) and diabetes mellitus (Inomata, S. et al, Bone Mineral 1, 187–192 (1986)) has been suggested. Another indication for 1,25$(OH)_2D_3$ is suggested by the recent observation of an association between hereditary vitamin D resistance and alopecia: treatment with 1,25$(OH)_2D_3$ may promote hair growth (Editorial, Lancet, Mar. 4, 1989, p. 478). Also, the fact that topical application of 1,25$(OH)_2D_3$ reduces the size of sebaceous glands in the ears of male Syrian hamsters suggests that this compound might be useful for the treatment of acne (Malloy, V. L. et al., the Tricontinental Meeting for Investigative Dermatology, Washington, 1989).

However, the therapeutic possibilities in such indications of 1,25$(OH)_2D_3$ are severely limited by the well known potent effect of this hormone on calcium metabolism; elevated blood concentrations will rapidly give rise to hypercalcemia. Thus, this compound and its potent synthetic analogues are not completely satisfactory for use as drugs in the treatment of e.g. psoriasis, cancer or immune diseases which may require continuous administration of the drug in relatively high doses.

A number of oxa- and thia-analogues of vitamin $D_3$ are known, including the 24-oxa-analogue of 24a-homo-1α,25-dihydroxy-vitamin $D_3$ and its 26,27-dialkyl derivatives (European Patent Appln. No. 450 743A). The oxa-compounds of the present invention differ structurally from these compounds in that they have the oxygen atom situated at a different position, i.e. 24a or 24b, in a further elongated side chain and/or in that they possess the epi-configuration at the 20-position. In addition a number of 23-oxa and 23-thia compounds have been described (International patent application No. PCT/DK91/00091). Again these are structurally distinct from the compounds of the present invention in that they do not contain an oxygen or sulphur linking atom at position 24 or further out (i.e. 24a or 24b) in the side chain.

The usefulness of a vitamin D analogue in the above mentioned indications is dependent not only upon a high activity demonstrated in an in vitro cell differentiation test, but also upon the fate of the compound in the organism.

It has now been found that the compounds of the present invention show favourable selectivity with respect to their effects on cell differentiation in vitro and their calcemic effects in vivo, and at the same time show high bioavailability as well as chemical and metabolic stability.

The selectivity of the compounds is illustrated by the fact that while the concentration needed to induce cell differentiation in a human monocytic rumour cell line is the same as or considerably lower than that needed of 1,25$(OH)_2D_3$ to give the same effect, in vivo in rats the compounds are less active than 1,25$(OH)_2D_3$ in inducing hypercalciuria and hypercalcemia.

The compounds of the invention are therefore especially suited for both local and systemic treatment and prophylaxis of human and veterinary disorders which are characterized by 1) abnormal cell proliferation and/or cell differentiation, such as certain dermatological disorders including psoriasis and certain cancer forms, 2) an imbalance in the immune system, e.g. in autoimmune diseases, including diabetes mellitus, host versus graft reaction, and rejection of transplants; and additionally for the treatment of inflammatory diseases, such as rheumatoid arthritis and asthma. Acne, alopecia, and hypertension are other conditions which may be treated with the compounds of the invention. Finally, as thickening of the skin is observed after topical treatment with the compounds of the invention, these compounds may be useful for treatment or prevention of skin ageing, including photo-ageing.

Because of the low tendency of the compounds to produce hypercalcemia on continued administration they are expected to be valuable for the long term treatment of hyperparathyroidism (particularly secondary hyperparathyroidism associated with renal failure) and for promoting osteogenesis and treating osteoporosis. For these indications the presently described compounds have a higher therapeutic ratio than the prior art compounds.

The present compounds may be used in combination with other pharmaceuticals. In the prevention of graft rejection and graft versus host reaction, a treatment with the present compounds may advantageously be combined with a cyclosporin treatment.

The compounds of formula I may conveniently be prepared from the vitamin D-derivative 1 (Tetrahedron, 43, 4609 (1987)) for example by the routes outlined in Scheme 1. The routes used to prepare the key intermediates II, some of which are known compounds, are not indicated on the Scheme, but some are illustrated in the preparations.

The symbol "◻" next to a carbon atom (cf. formula I) indicates than this methylene ($^\square CH_2$) may optionally be replaced by a radical of the same valency, as illustrated in the Preparations, Tables 1 and 2. In formulas II through VIII, n=0, 1 or 2, and the symbol Q is a surrogate for atoms 22 and 23, i.e. $^{22H}CH_2$–$^{23H}CH_2$ of I or a group that can be converted to it.

The following standard abbreviations are used throughout this disclosure: Me=methyl; Et=ethyl; Pr$^n$=n-propyl; Pr$^i$= isopropyl; Bu$^t$=tert-butyl=t-butyl; THP =tetra-hydro-4H-pyran-2-yl; THF=tetrahydrofuran: Ts=p-toluenesulphonyl; TBA=tetra-(n-butyl)-ammonium; TBDMS=tert-butyldimethylsilyl; DMF=N,N-dimethylformamide.

Scheme 1

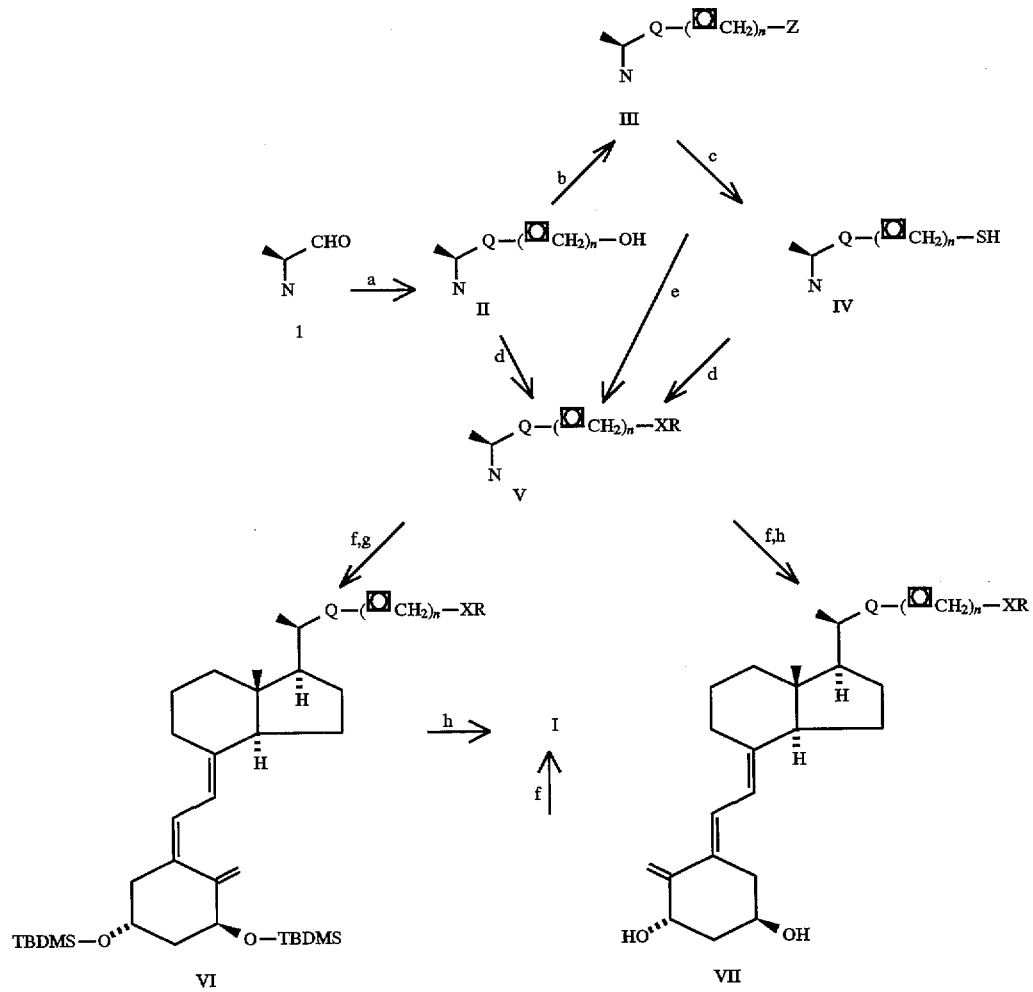

-continued
Scheme 1

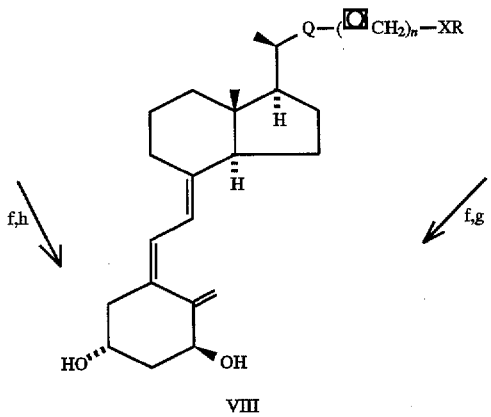

VIII

Notes to Scheme 1
a) Several steps: see Preparations.
b) Conversion of OH to a leaving group (e.g. by tosylation for Z = OTs or bromination for Z = Br).
c) (i) Nucleophilic substitution with thioacetate, (ii) basic hydrolysis.
d) Alkylation with the side chain building block R-Z in the presence of base (e.g. NaOH, KOBu$^t$, NaH or KH), with or without catalyst (e.g. 18-Crown-6, TBA bromide) in anhydrous solvent (e.g. DMF or THF), or under phase transfer conditions (e.g. toluene - water).
e) Reaction with the side chain building block R-XH in the presence of base (e.g. NaOH, KOBu$^t$, NaH or KH), with or without catalyst (e.g. 18-Crown-6, TBA bromide) in anhydrous solvent (e.g. DMF or THF), or under phase transfer conditions (e.g. toluene - water).
f) Optional functional group modification in the side chain.
g) Isomerisation with hv- triplet sensitizer, e.g. anthracene.
h) Deprotection with TBA$^+$F$^-$ or HF.

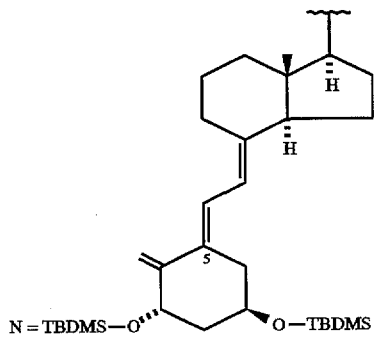

It should be noted that although the shown intermediates may have hydroxyl groups protected as tert-butyl-dimethylsilyl ethers, the scope of the invention does not exclude the use of alternative hydroxyl protecting groups well known in the art (such as those described in T. W. Greene, "Protective groups in organic synthesis", Wiley, New York, 1981), together with alternative reactions for deprotection.

O-Alkylation of II or S-alkylation of IV to give V (X=O from II; X=S from IV) is achieved by treatment under basic conditions with a side chain building block of general formula Z-R, in which Z is a leaving group such as a halogen (Cl, Br or I) or p-toluenesulphonyloxy or trifluoromethanesulphonyloxy, and R is —($^n$CH$_2$)$_m$—$^{25}$C(OH)—(R')$_2$, in which R' is methyl or ethyl, and m=1 or 2, as appropriate ultimately to complete the side chain of I (such that "—($^n$CH$_2$)$_n$—X—($^n$CH$_2$)$_m$—" corresponds to "U"), or optionally a radical which can be converted to this at any convenient later stage (or over several stages). Thus R in compounds V, VI, VII and VIII does not necessarily have the same meaning along a particular synthetic sequence. The conversion of R into —($^n$CH$_2$)$_m$—$^{25}$C(OH)—(R')$_2$ may well involve several steps and possibly involve a temporary protection of the sensitive triene system of the molecule, e.g. as the cyclo-adduct formed with sulphur dioxide. An alternative to this route involves treatment of the intermediate III (Z is a leaving group as described above) under basic conditions with a side chain building block HX-R, in which X is oxygen or sulphur and R is as described above, to give the intermediate V. Apart from any necessary modification within the side chain residue (R), the conversion of V to I involves a photoisomerisation step and a desilylation step, analogous to the steps used in the last stages of the synthesis of other vitamin D analogues (see European patent No. 0 227 826).

It may be convenient to change the order of the alkylation reaction (d or e) and the photoisomerisation reaction (g), in which case the (5Z)-isomer of II, III, or IV is an intermediate.

The side chain building blocks, RZ, are either known compounds (several are described in international patent application PCT/DK89/00079) or may be prepared analogously to those described in PCT/DK89/00079. The R-Z is typically Br—($^n$CH$_2$)$_m$—$^{25}$C(OY)—(R')$_2$ in which Y is a hydroxyl protecting group, e.g. tetrahydropyranyloxy or trialkylsilyloxy. (Any such THP ethers R-Z, which are not described in PCT/DK89/00079, are readily prepared from the corresponding alcohol).

The side chain building blocks HX-R are also known compounds or may be prepared by methods analogous to those used to prepare such known compounds. The synthesis of new compounds R-Z or HX-R are illustrated in the Preparations. For the case when m=1 R-Z may be Br—$CH_2CO_2Bu^t$, and HX-R may be $HSCH_2CO_2Et$, and the ester group is converted by reaction e.g. with a Grignard reagent to $^{25}C$—$(R')_2OH$.

As schematized above, at least for the "24-thia" compounds the route does not exclude deferring the alkylation of a thiol even as far as the last step (e.g.) VIII, R=M→I).

The present compounds are intended for use in pharmaceutical compositions which are useful in the treatment of human and veterinary disorders as described above.

The amount required of a compound of formula I (hereinafter referred to as the active ingredient) for therapeutic effect will, of course, vary both with the particular compound, the route of administration and the mammal under treatment. The compounds of the invention can be administered by the parenteral, intra-articular, enteral or topical routes. They are well absorbed when given enterally and this is the preferred route of administration in the treatment of systemic disorders. In the treatment of dermatological disorders like psoriasis, topical or enteral forms are preferred.

In the treatment of respiratory diseases like asthma an aerosol is preferred.

While it is possible for an active ingredient to be administered alone as the raw chemical, it is preferable present it as a pharmaceutical formulation. Conveniently, the active ingredient comprises from 1 ppm to 0.1% by weight of the formulation.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and for human medical use, of the present invention comprise an active ingredient in association with a pharmaceutically acceptable carrier therefore and optionally other therapeutic ingredient (s). The carrier(s) must be "acceptable" in the sense of being compatible with the other ingredients of the formulations and not deleterious to the recipient thereof.

The formulations include e.g. those in a form suitable for oral, rectal, parenteral (including subcutaneous, intramuscular and intravenous), intra-articular and topical administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

A tablet may be made by compressing or moulding the active ingredient optionally with one or more accessory ingredients. Compressed tablets may be prepared by compressing, in a suitable machine, the active ingredient in a free-flowing form such as a powder or granules, optionally mixed by a binder, lubricant, inert diluent, surface active or dispersing agent. Moulded tablets may be made by moulding, in a suitable machine, a mixture of the powdered active ingredient and suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical administration, including topical application to the eye, include liquid or semi-liquid preparations such as liniments, lotions, applicants, oil-in-water or water-in-oil emulsions such as creams, ointments or pastes; or solutions or suspensions such as drops.

For asthma treatment inhalation of powder, self-propelling or spray formulations, dispensed with a spray can, a nebulizer or an atomizer can be used. The formulations, when dispensed, preferably have a particle size in the range of 10 to 100 μ.

Such formulations are most preferably in the form of a finely comminuted powder for pulmonary administration from a powder inhalation device or self-propelling powder-dispensing formulations. In the case of self-propelling solution and spray formulations, the effect may be achieved either by choice of a valve having the desired spray characteristics (i.e. being capable of producing a spray having the desired particle size) or by incorporating the active ingredient as a suspended powder in controlled particle size. These self-propelling formulations may be either powder-dispensing formulations or formulations dispensing the active ingredient as droplets of a solution or suspension.

Self-propelling powder-dispensing formulations preferably comprise dispersed particles of solid active ingredients, and a liquid propellant having a boiling point below 18° C. at atmospheric pressure. The liquid propellant may be any propellant known to be suitable for medicinal administration and may comprise one or more $C_1$–$C_6$-alkyl hydrocarbons or halogenated $C_1$–$C_6$-alkyl hydrocarbons or mixtures thereof; chlorinated and fluorinated $C_1$–$C_6$-alkyl hydrocarbons are especially preferred. Generally, the propellant constitutes 45 to 99.9% w/w of the formulation whilst the active ingredient constitutes 1 ppm to 0.1% w/w, of the formulation.

In addition to the aforementioned ingredients, the formulations of this invention may include one or more additional ingredients such as diluents, buffers, flavouring agents, binders, surface active agents, thickeners, lubricants, preservatives, e.g. methyl hydroxybenzoate (including antioxidants), emulsifying agents and the like. The compositions may further contain other therapeutically active compounds usually applied in the treatment of the above mentioned pathological conditions.

The present invention further concerns a method for treating patients suffering from one of the above pathological conditions, said method consisting of administering to a patient in need of treatment an effective amount of one or more compounds of formula I, alone or in combination with one or more other therapeutically active compounds usually applied in the treatment of said pathological conditions. The treatment with the present compounds and/or with further therapeutically active compounds may be simultaneous or with intervals.

In the treatment of systemic disorders daily doses of from 0.1–100 µg, preferably from 0.2–25 µg, of a compound of formula I are administered. In the topical treatment of dermatological disorders, ointments, creams or lotions containing from 0.1–500 µg/g, and preferably from 1–100 µg/g, of a compound of formula I are administered. The oral compositions are formulated, preferably as tablets, capsules, or drops, containing from 0.05–50 µg, preferably from 0.1–25 µg, of a compound of formula I, per dosage unit.

The invention will now be further described in the following non-limiting Preparations and Examples:

PREPARATIONS AND EXAMPLES

General

The exemplified compounds I are listed in Table 1. The intermediates of Scheme I referred to in the Preparations are to be identified by numbers with the corresponding formulae in Table 2. These are used to illustrate typical syntheses of the exemplified compounds I.

For nuclear magnetic resonance spectra (300 MHz) chemical shift values (δ) are quoted in ppm for deuteriochloroform solutions (except where otherwise stated) relative to internal tetramethylsilane (δ=0) or chloroform (δ=7.25). The value for a multiplet, either defined (doublet (d), triplet (t), quartet (q)) or not (m) at the approximate mid point is given unless a range is quoted (s=singlet, b=broad). Coupling constants (J) are given in Hertz, and are sometimes approximated to the nearest unit.

Ether is diethyl ether, and was dried over sodium. THF was dried over sodium-benzophenone. Petroleum ether refers to the pentane fraction. If not specified, % means v/v %. Reactions were run at room temperature unless otherwise noted. The work-up procedure referred to involves dilution with the specified solvent (otherwise the organic reaction solvent), extraction with water and then brine, drying over anhydrous $MgSO_4$, and concentration in vacuo to give a residue. Chromatography was performed on silica gel.

TABLE 1

Examples of Compounds of formula I (Details are provided for compounds where an Example Number is given; the other compounds may be prepared using analogous reaction sequences).

| Compound No. | Ex. No. | Surrogate for methylene- -22 | -23 | U | R' |
|---|---|---|---|---|---|
| 101 | 1 | $CH_2$ | $CH_2$ | $O-CH_2$ | Me |
| 102 | 2 | $CH_2$ | $CH_2$ | $O-CH_2$ | Et |
| 103 | 3 | $CH_2$ | $CH_2$ | $O-CH_2-CH_2$ | Et |
| 104 | 4 | $CH_2$ | $CH_2$ | $O-CH_2-CF_2$ | Et |
| 107 | 5 | $CH_2$ | $CH_2$ | $S-CH_2$ | Me |
| 106 | 6 | $CH_2$ | $CH_2$ | $S-CH_2$ | Et |
| 105 | 7 | CH* | CH* | $CH_2-O-CH_2$ | Me |
| 108 | 8 | $CH_2$ | $CH_2$ | $CH_2-O-CH_2$ | Me |
| 109 | — | O | $CH_2$ | $CH_2-O-CH_2$ | Me |
| 110 | — | $CH_2$ | O | $CH_2-CH_2-O-CH_2$ | Me |
| 111 | — | $CH_2$ | $CH_2$ | $S-CH_2-CH_2$ | Et |
| 112 | — | $CH_2$ | $CH_2$ | $S-CH_2-CF_2$ | Et |
| 113 | — | $CH^+$ | $CH^+$ | $CH_2-O-CH_2$ | Me |

*(E) configuration of 22,23-double bond.
+(Z) configuration of 22,23-double bond.

TABLE 2

Examples of intermediates of formula II through VIII (Scheme 1) (Details are provided for compounds where a Preparation Number is given; the other compounds may be prepared using analogous reaction sequences when not otherwise noted)

| Compound No. | Prep. No. | Type | Q | $(^*CH_2)_n$ | XR or Z |
|---|---|---|---|---|---|
| 4 | 1C | II | $CH_2-CH_2$ | — | — |
| 7 | 2C | II | $CH_2-CH_2$ | $CH_2$ | — |
| 10 | 3C | II | $CH_2-CH_2$ | $CH_2-CH_2$ | — |
| 11 | —* | II | $CH=CH*$ | $CH_2$ | — |
| 12 | 4 | III | $CH_2-CH_2$ | — | OTs |
| 13 | 5 | III | $CH_2-CH_2$ | $CH_2$ | OTs |
| 14 | 6 | V | $CH_2-CH_2$ | — | $O-CH_2CO_2Bu^t$ |
| 15 | 10 | V | $CH_2-CH_2$ | — | $O-CH_2-C(OH)Me_2$ |
| 16 | 11 | V | $CH_2-CH_2$ | — | $O-CH_2-C(OH)Et_2$ |
| 17 | 8 | V | $CH_2-CH_2$ | — | $O-CH_2-CH_2C(OH)Et_2$ |
| 18 | 9 | V | $CH_2-CH_2$ | — | $O-CH_2CF_2-C(OH)Et_2$ |
| 19 | 7 | V | $CH=CH*$ | $CH_2$ | $O-CH_2-CO_2Bu^t$ |
| 20 | 12 | V | $CH=CH*$ | $CH_2$ | $O-CH_2-C(OH)Me_2$ |
| 21 | 13 | VI | $CH_2-CH_2$ | — | $O-CH_2-C(OH)Me_2$ |

TABLE 2-continued

Examples of intermediates of formula II through VIII (Scheme 1) (Details are provided for compounds where a Preparation Number is given; the other compounds may be prepared using analogous reaction sequences when not otherwise noted)

| Compound No. | Prep. No. | Type | Q | (*CH$_2$)$_n$ | XR or Z |
|---|---|---|---|---|---|
| 22 | 14 | VI | CH$_2$—CH$_2$ | — | O—CH$_2$—C(OH)Et$_2$ |
| 23 | 15 | VI | CH$_2$—CH$_2$ | — | O—CH$_2$CH$_2$—C(OH)Et$_2$ |
| 24 | 16 | VI | CH$_2$—CH$_2$ | — | O—CH$_2$CF$_2$—C(OH)Et$_2$ |
| 25 | 17 | VI | CH=CH* | CH$_2$ | O—CH$_2$—C(OH)Me$_2$ |
| 26 | 24 | V | CH$_2$—CH$_2$ | — | S—CH$_2$—C(OH)Et$_2$ |
| 27 | 26 | VI | CH$_2$—CH$_2$ | — | S—CH$_2$C(OH)Et$_2$ |
| 28 | 18 | II | O—CH$_2$ | CH$_2$ | — |
| 29 | — | V | O—CH$_2$ | CH$_2$ | O—CH$_2$—CO$_2$Bu$^t$ |
| 30 | — | V | O—CH$_2$ | CH$_2$ | O—CH$_2$—C(OH)Me$_2$ |
| 31 | — | VI | O—CH$_2$ | CH$_2$ | O—CH$_2$—C(OH)Me$_2$ |
| 32 | 19 | II | CH$_2$—O | CH$_2$—CH$_2$ | — |
| 33 | — | V | CH$_2$—O | CH$_2$—CH$_2$ | O—CH$_2$—CO$_2$Bu$^t$ |
| 34 | — | V | CH$_2$—O | CH$_2$—CH$_2$ | O—CH$_2$—C(OH)Me$_2$ |
| 35 | — | VI | CH$_2$—O | CH$_2$—CH$_2$ | O—CH$_2$—C(OH)Me$_2$ |
| 36 | 20 | III | CH$_2$—CH$_2$ | — | Br |
| 37 | 21 | III | CH$_2$—CH$_2$ | CH$_2$ | Br |
| 38 | 22 | V | CH$_2$—CH$_2$ | — | S—CH$_2$—CO$_2$Et |
| 39 | 23 | V | CH$_2$—CH$_2$ | — | S—CH$_2$—C(OH)Me$_2$ |
| 40 | 25 | VI | CH$_2$—CH$_2$ | — | S—CH$_2$—C(OH)Me$_2$ |
| 41 | 27 | V | CH$_2$—CH$_2$ | CH$_2$ | O—CH$_2$—CO$_2$Bu$^t$ |
| 42 | 28 | V | CH$_2$—CH$_2$ | CH$_2$ | O—CH$_2$—C(OH)Me$_2$ |
| 43 | 29 | VI | CH$_2$—CH$_2$ | CH$_2$ | O—CH$_2$—C(OH)Me$_2$ |

The missing compound numbers refer to intermediates between compounds 1 and II and are described in the appropriate Preparations.
Previously described compound.
*(E) configuration of 22,23-double bond.

General Procedure 1

A: Conversion of a tosylate to a nitrile, followed by
B: Reduction to an aldehyde, and then C: Reduction to an alcohol of formula II (Preparations 1–3).

A: To a solution of the tosylate (7.50 mmol) in DMF (80 ml) at room temperature was added potassium cyanide (4.97 g, 76.2 mmol) and 18-Crown-6 (0.50 g, 1.89 mmol). After stirring for 5 h at 50° C. the reaction mixture was poured into water and extracted twice with ethyl acetate. The combined organic layers was washed several times with water, dried over MgSO$_4$ and concentrated. The residue was purified by chromatography (75 g silica gel; 5% EtOAc in petroleum ether as eluant) to give the nitrile.

B: To a solution of the nitrile from Part A (7 mmol) in dry ether (30 ml) at −78° C. was added a 1.0M solution of diisobutylaluminium hydride in toluene (9.0 ml). The reaction mixture was warmed to 0° C. After 2 h more diisobutylaluminium hydride (6.0 ml) was added and the mixture was stirred for an additional hour at 0° C. The mixture was quenched by saturated aq. NH$_4$Cl (5 ml) and methanol (5 ml) and extracted with ethyl acetate. The organic phase was washed with water (twice), and brine and then dried over MgSO$_4$ and concentrated in vacuo. Flash chromatography (75 g silica gel; 5% EtOAc in petroleum ether as eluant) to give the aldehyde.

C: A stirred, ice-cooled solution of the aldehyde from Part B (3.22 mmol) in THF (10 ml) and ethanol (35 ml) was treated with sodium borohydride (0.14 g, 3.54 mmol). After 30 minutes the reaction mixture was partitioned between ethyl acetate and water, and the organic layer was washed with brine and dried. Concentration in vacuo gave the alcohol of formula II.

Preparation 1A

1(S), 3(R)-bis-tert-butyldimethylsilyloxy-20(S)-cyanomethyl-9,10-secopregna-5(E), 7(E), 10(19)-triene (Compound 2)

The tosylate used is 1(S), 3(R)-bis-tert-butyldimethylsilyloxy-20(R)-(p-toluenesulphonyloxymethyl)-9,10-secopregna-5(E), 7(E), 10(19)-triene (5.47 g). Compound 2: δ 0.05 (m, 12H), 0.54 (s, 3H), 0.85 (s, 9H), 0.89 (s, 9H), 1.09 (d, 3H), 1.00–2.03 (m, 13H), 2.08 (bt, 1H), 2.31 (bd, 1H), 2.43 (m, 2H), 2.54 (dd, 1H), 2.88 (m, 1H), 4.21 (m, 1H), 4.52 (m, 1H), 4.94 (m, 1H), 4.98 (m, 1H), 5.82 (d, 1H), 6.43 (d, 1H).

Preparation 1B

1(S), 3(R)-bis-tert-butyldimethylsilyloxy-20(S)-formylmethyl-9,10-secopregna-5(E), 7(E), 10(19)-triene (Compound 3)

The nitrile used is compound 2 (4.06 g). Compound 3: δ 0.05 (m, 12H), 0.57 (s, 3H), 0.86 (s, 9H), 0.89 (s, 9H), 0.94 (d, 3H), 1.10–2.12 (m, 14H), 2.17–2.37 (m, 2H), 2.55 (dd, 1H), 2.65 (dd, 1H), 2.87 (dd, 1H), 4.21 (m, 1H), 4.53 (m, 1H), 4.93 (m, 1H), 4.98 (m, 1H), 5.83 (d, 1H), 6.44 (d, 1H), 9.74 (dd, 1H).

Preparation 1C

1(S), 3(R)-bis-tert-butyldimethylsilyloxy-20(S)-(2'-hydroxyethyl)-9,10-secopregna-5(E), 7(E), 10(19)-triene (Compound 4)

The aldehyde used is compound 3 (1.89 g). Compound 4: δ 0.05 (m, 12H), 0.56 (s, 3H), 0.85 (s, 9H), 0.89 (s, 9H), 0.86 (d, 3H), 1.10–2.10 (m, 17H), 2.30 (bd, 1H), 2.55 (dd, 1H), 2.87 (m, 1H), 3.55–3.80 (m, 2H), 4.21 (m, 1H), 4.53 (m, 1H), 4.93 (m, 1H), 4.98 (m, 1H), 5.82 (d, 1H), 6.45 (d, 1H).

Preparation 2A

1(S), 3(R)-bis-tert-butyldimethylsilyloxy-20(S)-(2'-cyanoethyl)-9,10-secopregna-5(E), 7(E), 10(19)-triene (Compound 5)

The tosylate used is 1(S), 3(S)-bis-tert-butyldimethylsilyloxy-20(S)-(2'-p-toluenesulphonyloxyethyl)-9,10-secopregna-5(E), 7(E), 10(19)-triene (Compound 12, Preparation 4) (5.57 g).

Preparation 2B

1(S), 3(R)-bis-tert-butyldimethylsilyloxy-20(S)-(2'-formylethyl)-9,10-secopregna-5(E), 7(E), 10(19)-triene (Compound 6)

The nitrile used is compound 5 (4.16 g). Compound 6: δ 0.05 (bs, 12H), 0.55 (s, 3H), 0.85 (d, 3H), 0.85 (s, 9H), 0.88 (s, 9H), 1.20–2.05 (m, 16H), 2.25–2.60 (m, 4H), 2.87 (dd, 1H), 4.20 (m, 1H), 4.52 (m, 1H), 4.93 (m, 1H), 4.97 (m, 1H), 5.81 (d, 1H), 6.44 (d, 1H), 9.77 (t, 1H).

Preparation 2C

1(S), 3(R)-bis-tert-butyldimethylsilyloxy-20(S)-(3'-hydroxy-1'-propyl)-9,10-secopregna-5(E), 7(E), 10(19)-triene (Compound 7H)

The aldehyde used is compound 6 (1.94 g). Compound 7: δ 0.05 (m, 12H), 0.53 (s, 3H), 0.85 (s, 9H), 0.89 (s, 9H), 0.86 (d, 3H), 1.15–2.05 (m, 19H), 2.30 (bd, 1H), 2.55 (dd, 1H), 2.87 (m, 1H), 3.55–3.70 (m, 2H), 4.21 (m, 1H), 4.53 (m, 1H), 4.93 (m, 1H), 4.98 (m, 1H), 5.82 (d, 1H), 6.45 (d, 1H).

Preparation 3A

1(S), 3 (R)-bis-tert-butyldimethylsilyloxy-20(S) -(3'-cyano-1'-propyl) -9,10-secopregna-5(E), 7(E), 10(19)-triene (Compound 8)

The tosylate used is 1(S),3(S)-bis-tert-butyldimethylsilyloxy-20(S)-(3'-p-toluenesulphonyloxy-1'-propyl)-9,10-secopregna- 5(E), 7(E), 10(19)-triene (Compound 13, Preparation 5) (5.68 g).

Preparation 3B

1(S), 3(R) -bis-tert-butyldimethylsilyloxy-20(S)-(3'-formyl-1'-propyl) -9,10-secopregna-5(E), 7(E), 10(19)-triene (Compound 9)

The nitrile used is compound 8 (4.26 g). Compound 9: δ 0.05 (bs, 12H), 0.55 (s, 3H), 0.85 (d, 3H), 0.85 (s, 9H), 0.88 (s, 9H), 1.05–2.05 (m, 18H), 2.35 (bd, 1H), 2.40 (m, 2H), 2.55 (dd, 1H), 2.87 (dd, 1H), 4.20 (m, 1H), 4.52 (m, 1H), 4.93 (m, 1H), 4.97 (m, 1H), 5.81 (d, 1H), 6.44 (d, 1H), 9.77 (t, 1H).

Preparation 3C:

1(S), 3(R) -bis-tert-butyldimethylsilyloxy-20(S)-(4'-hydroxy-1'-butyl)-9,10-secopregna-5(E), 7(E), 10(19)-triene (Compound 10)

The aldehyde used is compound 9 (1.98 g). Compound 10: δ 0.05 (m, 12H), 0.53 (s, 3H), 0.85 (s, 9H), 0.89 (s, 9H), 0.84 (d, 3H), 1.05–2.05 (m, 21H), 2.30 (bd, 1H), 2.55 (dd, 1H), 2.87 (m, 1H), 3.64 (t, 2H), 4.21 (m, 1H), 4.53 (m, 1H), 4.93 (m, 1H), 4.98 (m, 1H), 5.82 (d, 1H), 6.45 (d, 1H).

General Procedure 2

Conversion of an alcohol of formula II to a tosylate of formula III (Preparations 4 and 5)

The alcohol (1.19 mmol) was dissolved in dichloromethane (20 ml) and pyridine (1 ml), and the solution was stirred and ice-cooled during the addition of p-toluenesulphonyl chloride (0.81 g, 4.25 mmol). The reaction mixture was allowed to stand at room temperature overnight before being partitioned between ethyl acetate and water. The organic layer was washed consecutively with saturated cupric sulphate solution (twice), water, 5% sodium hydrogen carbonate solution, and brine, and then dried and concentrated in vacuo. Flash chromatography (50 g silica gel, 2% to 5% ethyl acetate in petroleum ether as eluant) to give the tosylate.

Preparation 4

1(S), 3(R)-bis-tert-butyldimethylsilyloxy-20(S)-(2'-p-toluenesulphonyloxyethyl)-9,10-secopregna-5(E), 7(E), 10(19)-triene (Compound 12)

The alcohol used is compound 4 (0.70 g). Compound 12: δ 0.05 (m, 12H), 0.47 (s, 3H), 0.77 (d, 3H), 0.85 (s, 9H), 0.89 (s, 9H), 1.10–2.05 (m, 16H), 2.29 (bd, 1H), 2.43 (s, 3H), 2.54 (dd, 1H), 2.85 (d, 1H), 4.08 (m, 2H), 4.20 (m, 1H), 4.52 (m, 1H), 4.93 (m, 1H), 4.97 (m, 1H), 5.80 (d, 1H), 6.43 (d, 1H), 7.33 (d, 2H), 7.78 (d, 2H).

Preparation 5

1(S),3(R)-bis-tert-butyldimethylsilyloxy-20(S)-(3'-p-toluenesulphonyloxy-1'-propyl)-9,10-secopregna-5(E),7(E), 10(19)-triene (Compound 13)

The alcohol used is compound 7 (0.72 g).

General Procedure 3

O-alkylation of Compounds II to give Compound V (Preparations 6, 7 and 27)

A mixture of the alcohol II (2.55 mmol), t-butyl bromoacetate (1.15 ml, 7.65 mmol) and a catalytic amount (200 mg) of tetra-n-butylammonium bromide was stirred vigorously overnight, at room temperature, in toluene (40 ml)/NaOH (aqueous, 20%, 30 ml). The reaction mixture was partitioned between ethyl acetate and water, and the organic layer was washed with brine, dried over $MgSO_4$, and evaporated in vacuo. Purification of the residue by chromatography (50 g silica gel, 5% EtOAc in petroleum ether as eluant) gave the compound V.

Preparation 6: Compound 14

The alcohol used is compound 4 (1.50 g). Compound 14: δ 0.05 (m, 12H), 0.55 (s, 3H), 0.85 (s, 9H), 0.89 (s, 9H), 0.82–0.92 (d, 3H), 1.47 (s, 9H), 1.00–2.10 (m, 16H), 2.30 (bd, 1H), 2.55 (dd, 1H), 2.86 (m, 1H), 3.53 (m, 2H), 3.93 (m, 2H), 4.21 (m, 1H), 4.53 (m, 1H), 4.93 (m, 1H), 4.97 (m, 1H), 5.81 (d, 1H), 6.44 (d, 1H).

Preparation 7: Compound 19

The alcohol used is compound 11 (1.53 g). Compound 19: δ 0.05 (m, 12H), 0.51 (s, 3H), 0.86 (s, 9H), 0.88 (s, 9H), 1.11 (d, 3H), 1.47 (s, 9H), 1.05–2.15 (m, 14H), 2.30 (bd, 1H), 2.55 (dd, 1H), 2.85 (m, 1H), 3.92 (s, 2H), 4.02 (m, 2H), 4.21 (m, 1H), 4.52 (m, 1H), 4.93 (m, 1H), 4.97 (m, 1H), 5.47 (m, 1H), 5.60 (dd, 1H), 5.80 (d, 1H), 6.44 (d, 1H).

General Procedure 4

Conversion of Compounds III to Compounds V (Preparations 8, 9, 18, 19 and 22)

Method A (X=O)

To a solution of the side chain building block R-XH (0.372 mmol), potassium hydride (0.187 ml, 20% suspension in oil) and 18-Crown-6 (98 mg) in dry THF (6 ml), the compound III (0.186 mmol) is added. The mixture is stirred at room temperature overnight, diluted with ethyl acetate and extracted twice with water and brine. After drying over MgSO$_4$ and the removal of solvent in vacuo, the product is purified by chromatography (30 g silica gel; 10% EtOAc in petroleum ether as eluant) to give the compound V.

Method B (X=S):

Sodium hydride dispersion (55% in oil, 60 mg) was washed with petroleum ether (3×2 ml) under an atmosphere of argon. A solution of R-XH (0.82 mmol) in DMF (dried over molecular sieves) (2 ml) was added, followed by Compound III (ca. 0.5 mmol) in DMF (1 ml). After 30 minutes the reaction mixture was worked up with ether (60 ml). The residue was purified by chromatography to give V.

Preparation 8: Compound 17

Using method A, the side chain building block R-XH is 3-ethyl-1,3-pentanediol (91 mg), and the compound III is compound 12 (139 mg). Compound 17: δ 0.05 (s, 12H), 0.54 (s, 3H), 0.85 (s, 9H), 0.89 (s, 9H), 0.80–0.90 (m, 9H), 1.51 (m, 4H), 1.71 (t, 2H), 0.75–2.10 (m, 16H), 2.30 (bd, 1H), 2.55 (dd, 1H), 2.86 (m, 1H), 3.22 (s, 1H), 3.44 (m, 2H), 3.62 (m, 2H), 4.21 (m, 1H), 4.52 (m, 1H), 4.93 (m, 1H), 4.97 (m, 1H), 5.81 (m, 1H), 6.44 (d, 1H).

4,4-difluoro-3-ethyl-3-trimethylsilyloxy-5-hexene

A heterogenous solution of acid-washed zinc powder (4.74 g, 72.5 mmol), 3-pentanone (3.84 ml, 36.4 mmol), and dry THF (25 ml) was cooled to 0° C. in an ice-water bath, and a mixture of 3-bromo-3,3-difluoropropene (6.00 g, 38.2 mmol) in dry THF (10 ml) was slowly added. The reaction mixture was allowed to stand at room temperature overnight. Then, aqueous hydrochloric acid (5%, 30 ml) was added to the reaction mixture, which was stirred for 5 minutes. Excess zinc was removed by filtration and washed with ether. The organic phase was washed with saturated sodium bicarbonate solution, water (twice), dried over MgSO$_4$ and concentrated. This oil was dissolved in dichloromethane (50 ml), and triethylamine (7.05 ml, 50.8 mmol) and 4-(N,N-dimethylamino)-pyridine (250 mg) are added. The reaction mixture was cooled to 0° C. and trimethylsilyl chloride (6.42 ml, 50.8 mmol) was added dropwise, and the mixture was stirred at room temperature overnight. The reaction mixture was poured into water and extracted twice with ether. The combined organic layers were washed several times with water, dried over MgSO$_4$, and evaporated in vacuo. The residue was purified by chromatography (50 g silica gel; 2% EtOAc in petroleum ether as eluant) to give the compound as a colourless oil. δ 0.13 (s, 9H), 0.89 (m, 6H), 1.5–1.8 (m, 4H), 5.43 (m, 1H), 5.63 (m, 1H), 5.92–6.13 (m, 1H).

2,2-difluoro-3-ethyl-3-trimethylsilyloxy-pentanal 4,4-difluoro-3-ethyl-3-trimethylsilyloxy-5-hexene (2.00 g, 8.88 mmol) was dissolved in dichloromethane (80 ml), and the solution was cooled to −78° C. A gaseous mixture of O$_3$ in O$_2$ was passed into the solution until it became blue. Nitrogen was bubbled through the solution to remove excess ozone, dimethyl sulfide (3 ml) was added, and the solution was brought slowly to room temperature. Following ozonide decomposition, dichloromethane was added, and the organic layer was washed with water (twice), dried over CaCl$_2$ and concentrated under reduced pressure. Flash chromatography (50 g silica gel; 5% EtOAc in petroleum ether as eluant) to give the title compound as a pale yellow oil. δ 0.14 (s 9H), 0.91 (m, 6H), 1.64 (m, 2H), 1.85 (m, 2H), 9.55 (t, 1H).

2,2-difluoro-3-ethyl-3-trimethylsilyloxy-pentane-1-ol

A stirred, ice-cooled solution of 2,2-difluoro-3-ethyl-3-trimethylsilyloxy-pentanal (1.45 g, 6.08 mmol) in THF (5 ml) and ethanol (15 ml) was treated with sodium borohydride (2.76 mg, 7.30 mmol). After 30 minutes the reaction mixture was partitioned between ethyl acetate and water, and the organic layer was washed with brine, dried over MgSO$_4$ and concentrated. Flash chromatography (50 g silica gel; 10% EtOac in petroleum ether as eluant) afforded the title compound as a colourless oil, δ 0.15 (s, 9H), 1.36 (t, 6H), 2.48 (m, 1H), 3.93 (m, 2H).

Preparation 9: Compound 18

Using method A, the side chain building block R-XH is 2,2-difluoro-3-ethyl-3-trimethylsilyloxy-pentane-1-ol (289 mg) and the compound III is compound 12 (200 mg). The isolation procedure gave rise to desilylation in the side chain.

Compound 18: δ 0.05 (s, 12H), 0.54 (s, 3H), 0.86 (d, 3H), 0.86 (s, 9H), 0.90 (s, 9H), 0.93 (t, 6H), 1.10–2.10 (m, 20H), 2.30 (bd, 1H), 2.55 (dd, 1H), 2.62 (s, 1H), 2.87 (m, 1H), 3.57 (m, 2H), 3.79 (m, 2H), 4.21 (m, 1H), 4.53 (m, 1H), 4.94 (m, 1H), 4.98 (m, 1H), 5.81 (m, 1H), 6.44 (d, 1H).

General Procedure 5

Modification of "XR" in Compounds V: Reaction of an ester function within "R" with an organometallic reagent to give an alcohol (Preparations 10, 11, 12, 23, 24 and 28)

To a solution of the ester V (0.306 mmol) in dry ether (5 ml) at −40° C. was added dropwise the organometallic reagent. The mixture was stirred at −40° C. for ½ h and at 0° C. for 1 h. The reaction mixture is poured into a stirred ice-cooled mixture of ether (25 ml) and ammonium chloride (1.5 g) in water (10 ml). The ether layer is separated, and the aqueous layer is extracted with more ether (2×50 ml). The combined ether layers are washed consecutively with water (2×50) and saturated aqueous sodium chloride (50 ml), dried and concentrated in vacuo. Flash chromatography (30 g silica gel, 10% increasing to 30% ether in petroleum ether as eluant) gave the alcohol V.

Preparation 10: Compound 15

The ester V is compound 14 (215 mg), and the organometallic reagent is MeMgBr (3M solution in ether, 1.0 ml). Compound 15: δ 0.05 (m, 12H), 0.55 (s, 3H), 0.85 (s, 9H), 0.86 (d, 3H), 0.89 (s, 9H), 1.19 (s, 6H), 1.00–2.10 (m, 16H), 2.30 (bd, 1H), 2.32 (s, 1H), 2.55 (dd, 1H), 2.87 (m, 1H), 3.22 (m, 2H), 3.50 (m, 2H), 4.21 (m, 1H), 4.53 (m, 1H), 4.93 (m, 1H), 4.98 (m, 1H), 5.82 (d, 1H), 6.45 (d, 1H).

Preparation 11: Compound 16

The ester V is compound 14 (215 mg), and the organometallic reagent is EtMgBr (3M solution in ether, 1.0 ml). Compound 16: δ 0.05 (m, 12H), 0.55 (s, 3H), 0.85 (s, 9H), 0.89 (s, 9H), 0.82–0.92 (m, 9H), 1.50 (m, 4H), 1.10–2.10 (m, 16H), 2.13 (s, 1H), 2.31 (bd, 1H), 2.55 (dd, 1H), 2.87 (m, 1H), 3.25 (m, 2H), 3.46 (m, 2H), 4.21 (m, 1H), 4.53 (m, 1H), 4.93 (m, 1H), 4.98 (m, 1H), 5.82 (d, 1H), 6.45 (d, 1H).

Preparation 12: Compound 20

The ester V is compound 19 (219 mg), and the organometallic reagent is MeMgBr (3M solution in ether, 1.0 ml). Compound 20: δ 0.05 (m, 12H), 0.51 (s, 3H), 0.86 (s, 9H), 0.88 (s, 9H), 0.94 (d, 3H), 1.18 (s, 6H), 1.15–2.15 (m, 14H), 2.30 (bd, 1H), 2.55 (dd, 1H), 2.85 (m, 1H), 3.22 (s, 2H), 3.96 (m, 2H), 4.21 (m, 1H), 4.52 (m, 1H), 4.93 (m, 1H), 4.97 (m, 1H), 5.47 (m, 1H), 5.54 (dd, 1H), 5.80 (d, 1H), 6.43 (d, 1H).

General Procedure 6

Isomerization of Compounds V to the Corresponding Compounds VI (Preparations 13 to 17, 25, 26 and 29)

A solution of the compound V (ca. 0.2 g), anthracene (200 mg) and triethylamine (0.3 ml) in dichloromethane (15 ml) under nitrogen in a Pyrex flask was irradiated with light from a high pressure ultraviolet lamp, type TQ718Z2 (Hanau) at about 10° C. for 30 minutes. The reaction mixture was filtered, concentrated in vacuo and purified by chromatography to give the compound VI.

Preparation 13: Compound 21

The compound V is compound 15, and the chromatographic conditions were: 30 g silica gel, 10% ether in petroleum ether as eluant. Compound 21: δ 0.05 (m, 12H), 0.54 (s, 3H), 0.87 (s, 18H), 0.82–0.92 (d, 3H), 1.19 (s, 6H), 1.10–2.05 (m, 16H), 2.20 (dd, 1H), 2.32 (s, 1H), 2.44 (dd, 1H), 2.82 (m, 1H), 3.23 (m, 2H), 3.50 (m, 2H), 4.18 (m, 1H), 4.36 (m, 1H), 4.86 (m, 1H), 5.17 (m, 1H), 6.01 (d, 1H), 6.23 (d, 1H).

Preparation 14: Compound 22

The compound V is compound 16, and the chromatographic conditions were: 30 g silica gel, 10% ether in petroleum ether as eluant. Compound 22: δ 0.05 (m, 12H), 0.53 (s, 3H), 0.87 (s, 18H), 0.82–0.92 (m, 9H), 1.52 (m, 4H), 1.00–2.05 (m, 16H), 2.13 (s, 1H), 2.21 (dd, 1H), 2.44 (dd, 1H), 2.82 (m, 1H), 3.24 (m, 2H), 3.46 (m, 2H), 4.18 (m, 1H), 4.36 (m, 1H), 4.85 (m, 1H), 5.17 (m, 1H), 6.01 (d, 1H), 6.22 (d, 1H).

Preparation 15: Compound 23

The compound V is compound 17, and the chromatographic conditions were: 30 g silica gel, 10% ether in petroleum ether as eluant. Compound 23: δ 0.05 (m, 12H), 0.52 (s, 3H), 0.87 (s, 18H), 0.75–0.95 (m, 9H), 1.71 (t, 2H), 1.15–2.05 (m, 20H), 2.20 (dd, 1H), 2.43 (dd, 1H), 2.81 (m, 1H), 3.22 (bs, 1H), 3.43 (m, 2H), 3.61 (m, 2H), 4.18 (m, 1H), 4.36 (m, 1H), 4.85 (m, 1H), 5.17 (m, 1H), 6.00 (d, 1H), 6.22 (m, 1H).

Preparation 16: Compound 24

The compound V is compound 18, and the chromatographic conditions were: 30 g silica gel, 10% ether in petroleum ether as eluant. Compound 24: δ 0.05 (m, 12H), 0.53 (m, 3H), 0.87 (s, 18H), 0.88 (d, 3H), 0.92 (m, 12H), 1.10–2.10 (m, 20H), 2.21 (dd, 1H), 2.43 (dd, 1H), 2.63 (s, 1H), 2.82 (m, 1H), 3.56 (m, 2H), 3.80 (m, 2H), 4.18 (m, 1H), 4.36 (m, 1H), 4.85 (m, 1H), 5.17 (m, 1H), 6.00 (d, 1H), 6.22 (d, 1H).

Preparation 17: Compound 25

The compound V is compound 20, and the chromatographic conditions were: 30 g silica gel, 10% increasing to 30% ether in petroleum ether as eluant. Compound 25: δ 0.05 (m, 12H), 0.54 (s, 3H), 0.87 (s, 18H), 0.94 (d, 3H), 1.18 (s, 6H), 1.10–2.15 (m, 14H), 2.20 (dd, 1H), 2.32 (s, 1H), 2.44 (dd, 1H), 2.82 (m, 1H), 3.22 (s, 2H), 3.96 (m, 2H), 4.18 (m, 1H), 4.36 (m, 1H), 4.86 (m, 1H), 5.17 (m, 1H), 5.47 (m, 1H), 5.54 (dd, 1H), 6.01 (d, 1H), 6.23 (d, 1H).

Preparation 18: Compound 28

The compound was prepared by O-alkylation of 1(S), 3(R)-bis-tert-butyldimethylsilyloxy-20(R)-hydroxy-9,10-secopregna-5(E),7(E),10(19)-triene with KH and allyl bromide in THF followed by conversion of the product to the $SO_2$-adduct by reaction with liquid $SO_2$. Ozonolysis of the side chain double bond with reductive work-up ($O_3$ in $CH_2Cl_2$-MeOH followed by $NaBH_4$) and finally cleavage of the $SO_2$ ($NaHCO_3$, boiling ethanol) gave the title compound.

Preparation 19: Compound 32

This compound was prepared by the method of Preparation 18, but using 1(S),3(R)-bis-tert-butyldimethyl-silyloxy-20(R)-hydroxymethyl-9,10-secopregna-5(E),7(E),(10(19)-triene as starting material.

General Procedure 7

Conversion of an alcohol of formula II to a bromide of formula III (Preparations 20 and 21)

Triphenylphosphine (507 mg, 1.93 mmol) and pyridine (0.64 ml, 7.73 mmol) was added to a solution of the alcohol (ca. 1.5 mmol) in dichloromethane (10 ml) at 0° C. under an argon atmosphere. This was followed by dropwise addition of a carbon tetrabromide solution (640 mg, 1.93 mmol) in dichloromethane (10 ml) under stirring. After stirring for 1 hour at 25° C. the solvent is removed under reduced pressure and the residue washed with ethyl acetate/petroleum ether (2:8) (2×20 ml) to remove majority of $Ph_3PO$. The organic layer was washed with water and brine, dried over $MgSO_4$, and concentrated. The residue is purified by chromatography (30 g silica gel, 5% ethyl acetate in petroleum ether as eluant) to give the desired compound as an oil.

Preparation 20:

1(S), 3(R)-bis-tert-butyldimethylsilyloxy-20(S)-(2'-bromoethyl)-9,10-secopregna-5(E), 7(E), 10(19)-triene (Compound 36)

The alcohol used is compound 4 (0.90 g). Compound 36: δ 0.05 (m, 12H), 0.57 (s, 3H), 0.86 (s, 9H), 0.90 (s, 9H), 0.85–0.92 (d, 3H), 1.00–2.50 (m, 17H), 2.55 (dd, 1H), 2.88 (m, 1H), 3.30–3.58 (m, 2H), 4.21 (m, 1H), 4.53 (m, 1H), 4.94 (m, 1H), 4.98 (m, 1H), 5.82 (d, 1H), 6.45 (d, 1H).

Preparation 21

1(S), 3(R)-bis-tert-butyldimethylsilyloxy-20(S)-(3'-bromo-1'-propyl)-9,10-secopregna-5(E), 7(E), 10(19)-triene (Compound 37)

The alcohol used is compound 7 (0.90 g).

Preparation 22: Compound 38

Using General Procedure 4, method B, R-XH is ethyl mercaptoacetate (0.23 ml) and the compound III is compound 36 (918 mg).
Compound 38: δ 0.05 (m, 12H), 0.54 (s, 3H), 0.85 (s, 9H), 0.90 (s, 9H), 0.85–0.92 (d, 3H), 1.28 (t, 3H), 1.15–2.10 (m, 16H), 2.30 (bd, 1H), 2.55 (m, 2H), 2.72 (m, 1H), 2.86 (m, 1H), 3.20 (s, 2H), 4.18 (q, 2H), 4.20 (m, 1H), 4.52 (m, 1H), 4.93 (m, 1H), 4.97 (m, 1H), 5.82 (d, 1H), 6.44 (d, 1H).

Preparation 23: Compound 39

Using General Procedure 5, the ester V is compound 38 (200 mg), and the organometallic reagent is MeMgBr (3M solution in ether, 0.8 ml). Compound 39: δ 0.05 (m, 12H), 0.54 (s, 3H), 0.85 (s, 9H), 0.86 (d, 3H), 0.89 (s, 9H), 1.26 (s, 6H), 1.10–2.07 (m, 16H), 2.30 (bd, 1H), 2.36 (bs, 1H), 2.65 (s, 2H), 2.45–2.72 (m, 3H), 2.87 (m, 1H), 4.21 (m, 1H), 4.52 (m, 1H), 4.93 (m, 1H), 4.97 (m, 1H), 5.81 (d, 1H), 6.44 (d, 1H).

Preparation 24: Compound 26

Using General Procedure 5, the ester V is compound 38 (164 mg), and the organometallic reagent is EtMgBr (3M solution in ether, 0.64 ml). Compound 26: δ 0.05 (m, 12H), 0.54 (s, 3H), 0.86 (s, 9H), 0.90 (s, 9H), 0.84–0.90 (m, 9H), 1.15–2.10 (m, 20H), 2.15 (s, 1H), 2.30 (bd, 1H), 2.40–2.72 (m, 5H), 2.87 (m, 1H), 4.21 (m, 1H), 4.52 (m, 1H), 4.94 (m, 1H), 4.98 (m, 1H), 5.81 (d, 1H), 6.44 (d, 1H).

Preparation 25: Compound 40

Using General Procedure 6, the compound V is compound 39, and the chromatographic conditions were: 30 g silica gel, 5% increasing to 10% ethyl acetate in petroleum ether as eluant. Compound 40: δ 0.05 (m, 12H), 0.53 (s, 3H), 0.86 (s, 18H), 0.87 (d, 3H), 1.25 (s, 6H), 1.10–2.05 (m, 16H), 2.20 (dd, 1H), 2.38 (bs, 1H), 2.64 (s, 2H), 2.30–2.70 (m, 3H), 2.81 (m, 1H), 4.18 (m, 1H), 4.36 (m, 1H), 4.85 (m, 1H), 5.17 (m, 1H), 6.00 (d, 1H), 6.22 (d, 1H).

Preparation 26: Compound 27

Using General Procedure 6, the compound V is compound 26, and the chromatographic conditions were: 30 g silica gel, 2% increasing to 5% ethyl acetate in petroleum ether as eluant. Compound 27: δ 0.05 (m, 12H), 0.53 (s, 3H), 0.87 (s, 18H), 0.75–1.00 (m, 9H), 1.05–2.07 (m, 20H), 2.17 (bs, 1H), 2.20 (dd, 1H), 2.40–2.70 (m, 5H), 2.81 (m, 1H), 4.20 (m, 1H), 4.36 (m, 1H), 4.85 (m, 1H), 5.16 (m, 1H), 6.00 (d, 1H), 6.22 (d, 1H).

Preparation 27: Compound 41

Using General Procedure 3, the alcohol used is compound 7 (1.54 g). Compound 41: δ 0.05 (m, 12H), 0.52 (s, 3H), 0.85 (s, 9H), 0.85 (d, 3H), 0.89 (s, 9H), 1.47 (s, 9H), 1.05–2.05 (m, 16H), 2.30 (bd, 1H), 2.55 (dd, 1H), 2.86 (m, 1H), 3.48 (m, 2H), 3.93 (s, 2H), 4.21 (m, 1H), 4.53 (m, 1H), 4.93 (m, 1H), 4.97 (m, 1H), 5.81 (d, 1H), 6.44 (d, 1H).

Preparation 28: Compound 42

Using General Procedure 5, the ester V is compound 41 (219 mg), and the organometallic reagent is MeMgCl (3M solution in ether, 1.0 ml). Compound 42: δ 0.05 (m, 12H), 0.53 (s, 3H), 0.85 (s, 9H), 0.85 (d, 3H), 0.89 (s, 9H), 1.1–2.05 (m, 26H, including 1.19 (s, 6H)), 2.31 (bd, 1H), 2.33 (s, 1H), 2.55 (dd, 1H), 2.87 (m, 1H), 3.22 (s, 2H), 3.45 (t, 2H), 4.21 (m, 1H), 4.53 (m, 1H), 4.92 (m, 1H), 4.97 (m, 1H), 5.81 (d, 1H), 6.44 (d, 1H).

Preparation 29: Compound 43

Using General Procedure 6, the compound V is compound 42, and the chromatographic conditions were: 30 g silica gel, 10% ether in petroleum ether as eluant. Compound 43: δ 0.05 (m, 12H), 0.54 (s, 3H), 0.85 (d, 3H), 0.87 (s, 18H), 1.19 (s, 6H), 1.10–2.05 (m, 18H), 2.20 (dd, 1H), 2.33 (s, 1H), 2.44 (dd, 1H), 2.82 (m, 1H), 3.22 (s, 2H), 3.45 (t, 2H), 4.18 (m, 1H), 4.36 (m, 1H), 4.86 (m, 1H), 5.17 (m, 1H), 6.01 (d, 1H), 6.23 (d, 1H).

General Procedure 8A

Conversion of Compounds VI to the corresponding Compound I by desilylation with tetra-n-butylammonium fluoride (Examples 1–6)

A solution of Compound VI (0.3 mmol) and tetra-n-butylammonium fluoride trihydrate (1.2 mmol) in THF (10 ml) under $N_2$ was stirred at 60° C. for 1 hour. After cooling, the reaction mixture was partitioned between ethyl acetate and 2% sodium hydrogen carbonate solution. Work-up and purification by chromatography gave compound I.

General Procedure 8B

Conversion of Compounds VI to the corresponding Compound I by desilylation with HF (Examples 7 and 8)

The compound V (ca. 0.2 g) was dissolved in ethyl acetate (0.6 ml) and acetonitrile (8 ml) was added under vigorous stirring. A solution of 5% hydrofluoric acid in acetonitrile/water 8:1 (4.0 ml) was added, and the reaction mixture was stirred under nitrogen at room temperature for minutes. Excess 4N aqueous NaOH solution was added, and the reaction mixture was worked-up (ethyl acetate). The residue was purified by chromatography to give the compound I.

EXAMPLE 1

1(S), 3(R) -Dihydroxy-20(S)-[2-(2-hydroxy-2-methyl-1-propoxy) ethyl]-9,10-seco-pregna-5(Z), 7(E), 10(19)-triene (Compound 101)

Using Procedure 8A: the compound VI is compound 21, and the chromatographic conditions were: 30 g silica gel; 60% ethyl acetate in petroleum ether as eluant.
Compound 101: δ 0.56 (s, 3H), 0.86 (d, 3H), 1.20 (s, 6H), 1.10–2.40 (m, 20H), 2.60 (dd, 1H), 2.83 (m, 1H), 3.23 (m, 2H), 3.50 (m, 2H), 4.23 (m, 1H), 4.43 (m, 1H), 5.00 (m, 1H), 5.33 (m, 1H), 6.02 (d, 1H), 6.38 (d, 1H).

EXAMPLE 2

1(S),3(R)-Dihydroxy-20(S)-[2-(2-hydroxy-2-ethyl-1-butoxy)ethyl]-9,10-seco-pregna-5(Z),7(E),10(19)-triene (Compound 102).

Using Procedure 8A: the compound VI is compound 22, and the chromatographic conditions were: 30 g silica gel; 60% ethyl acetate in petroleum ether as eluant.
Compound 102: 0.56 (s, 3H), 0.85 (d, 3H), 0.86 (t, 6H), 1.15–2.10 (m, 22H), 2.15 (s, 1H), 2.31 (dd, 1H), 2.60 (dd, 1H), 2.83 (m, 1H), 3.26 (m, 2H), 3.47 (m, 2H), 4.23 (m, 1H), 4.43 (m, 1H), 5.00 (m, 1H), 5.33 (m, 1H), 6.02 (d, 1H), 6.38 (d, 1H).

EXAMPLE 3

1(S), 3(R) -Dihydroxy-20(S)-[2-(3-hydroxy-3-ethyl-1-pentoxy)ethyl]-9,10-seco-pregna-5(Z), 7(E), 10(19)-triene (Compound 103)

Using Procedure 8A: the compound VI is compound 23, and the chromatographic conditions were: 30 g silica gel; ethyl acetate in petroleum ether as eluant.
Compound 103: δ 0.55 (s, 3H), 0.85 (d, 3H), 0.86 (t, 6H), 1.72 (t, 2H), 1.15–2.25 (m, 22H), 2.31 (dd, 1H), 2.60 (dd, 1H), 2.83 (m, 1H), 3.24 (bs, 1H), 3.44 (m, 2H), 3.62 (m, 2H), 4.23 (m, 1H), 4.43 (m, 1H), 5.00 (m, 1H), 5.33 (m, 1H), 6.01 (d, 1H), 6.37 (d, 1H).

EXAMPLE 4

1(S), 3(R)-Dihydroxy-20(S) -[2-(3-hydroxy-3 -ethyl-2,2-difluoro-1-pentoxy)ethyl]-9,10-seco-pregna-5(Z), 7(E), 10(19)-triene (Compound 104)

Using Procedure 8A: the compound VI is compound 24, and the chromatographic conditions were: 30 g silica gel; 60% ethyl acetate in petroleum ether as eluant.
Compound 104: δ 0.54 (s, 3H), 0.85 (d, 3H), 0.93 (t, 6H), 1.15–2.10 (m, 22H), 2.29 (dd, 1H), 2.59 (m, 1H), 2.63 (s, 1H), 2.81 (m, 1H), 3.57 (m, 2H), 3.79 (m, 1H), 4.22 (m, 1H), 4.42 (m, 1H), 4.99 (m, 1H), 5.31 (m, 1H), 6.00 (d, 1H), 6.36 (d, 1H).

EXAMPLE 5

1(S), 3(R) -Dihydroxy-20(S)-[2-(2-hydroxy-2-methyl-1-propylthio)ethyl]-9,10-seco-pregna-5(Z), 7(E), 10(19)-triene (Compound 107)

21

Using Procedure 8A: the compound VI is compound 40, and the chromatographic conditions were: 15 g silica gel; 60% ethyl acetate in petroleum ether as eluant. Compound 107: δ 0.56 (s, 3H), 0.86 (d, 3H), 1.27 (s, 6H), 1.10–2.07 (m, 18H), 2.31 (dd, 1H), 2.40 (bs, 1H), 2.66 (s, 2H), 2.45–2.72 (m, 3H), 2.83 (m, 1H), 4.23 (m, 1H), 4.43 (m, 1H), 5.00 (m, 1H), 5.33 (m, 1H), 6.02 (d, 1H), 6.37 (d, 1H).

EXAMPLE 6

1(S), 3(R) -Dihydroxy-20(S)-[2-(2-hydroxy-2-ethyl-1-butylthio)ethyl]-9,10-seco-pregna-5(Z), 7(E), 10(19)-triene (Compound 106)

Using Procedure 8A: the compound VI is compound 27, and the chromatographic conditions were: 15 g silica gel; 60% ethyl acetate in petroleum ether as eluant. Compound 106: δ 0.55 (s, 3H), 0.86 (d, 3H), 0.88 (t, 6H), 1.15–2.20 (m, 23H), 2.31 (dd, 1H), 2.45–2.70 (m, 5H), 2.83 (m, 1H), 4.23 (m, 1H), 4.43 (m, 1H), 5.00 (m, 1H), 5.33 (m, 1H), 6.02 (d, 1H), 6.38 (d, 1H).

EXAMPLE 7

1(S), 3(R)-Dihydroxy-20(S)-[3-(2-hydroxy-2-methyl-1-propoxy)-prop-1E-en-1-yl]-9,10-seco-pregna-5(Z), 7(E), 10(19)-triene (Compound 105)

Using Procedure 8B: the compound VI is compound 25, and the chromatographic conditions were: 30 g silica gel; ethyl acetate as eluant. Compound 105: δ 0.51 (s, 3H), 0.93 (d, 3H), 1.17 (s, 6H), 1.10–2.15 (m, 17H), 2.29 (bd, 1H), 2.56 (dd, 1H), 2.80 (bd, 1H), 3.21 (s, 2H), 3.96 (m, 2H), 4.20 (m, 1H), 4.41 (m, 1H), 4.98 (bt, 1H), 5.30 (m, 1H), 5.45 (m, 1H), 5.55 (m, 1H), 5.99 (d, 1H), 6.35 (d, 1H).

EXAMPLE 8

1(S), 3(R)-Dihydroxy-20(S)-[3-(2-hydroxy-2-methyl-1-propoxy)-prop-1-yl]-9,10-seco-pregna-5(Z), 7(E), 10(19)-triene (Compound 108)

Using Procedure 8B: the compound VI is compound 43, and the chromatographic conditions were: 30 g silica gel; ethyl acetate as eluant. Compound 108: δ 0.54 (s, 3H), 0.85 (d, 3H), 1.10–2.06 (m, 26H, including 1.20 (s, 6H)), 2.31 (m, 1H), 2.32 (s, 1H), 2.60 (dd, 1H), 2.83 (m, 1H), 3.23 (s, 2H), 3.45 (t, 2H), 4.23 (m, 1H), 4.43 (m, 1H), 5.00 (m, 1H), 5.33 (m, 1H), 6.02 (d, 1H), 6.38 (d, 1H).

EXAMPLE 9

Capsules Containing Compound 105

Compound 105 was dissolved in arachis oil to a final concentration of 10 μg compound 105/ml oil. 10 Parts by weight of gelatine, 5 parts by weight glycerine, 0.08 parts by weight potassium sorbate, and 14 parts by weight distilled water were mixed together with heating and formed into soft gelatine capsules. These were then filled each with 100 μl of the compound 105 in oil solution, such that each capsule contained 1 μg compound 105.

22

EXAMPLE 10

Dermatological Cream Containing Compound 105

In 1 g almond oil was dissolved 0.5 mg compound 105. To this solution was added 40 g of mineral oil and 20 g of self-emulsifying beeswax. The mixture was heated to liquify. After the addition of 40 ml hot water, the mixture was mixed well. The resulting cream contains approximately 5 μg of compound 105 per gram of cream.

What we claim is:

1. A compound of formula I

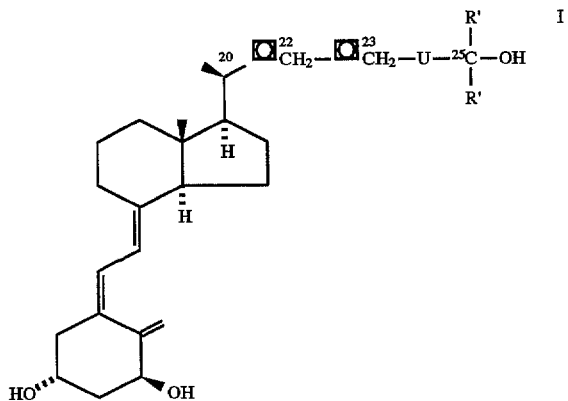

in which formula the "α" indicates that this carbon may be modified, and the moiety U replaces the 24-methylene of 1α,25-dihydroxy-20-epi-vitamin $D_3$ and stands for $(CH_2)_n$—Y—$(CH_2)_m$, where n is 0, 1 or 2, m is 1 or 2, and Y is oxygen or sulphur; and derivatives formed by replacing either the 22-methylene or the 23-methylene by an oxygen or by replacing 22- and 23-methylene with —CH=CH—; R' is methyl or ethyl; and in which one or more carbon atoms directly bonded to C-25 may optionally be substituted with one or more fluorine atoms; and derivatives of I in which one or more of the hydroxy groups are masked as groups which can be reconverted to hydroxy groups in vivo.

2. A compound of formula I according to claim 1 in which C-22 and C-23 are both carbon, m stands for 1 and Y is oxygen.

3. A compound according to claim 2 which is 1(S),3(R)-Dihydroxy-20(S)-[3-(2-hydroxy-2-methyl-1-propoxy)-prop-1E-en-1-yl]-9,10-seco-pregna-5(Z),7(E),10(19)-triene.

4. A diastereoisomer of a compound according to claim 1 in pure form.

5. A pharmaceutical composition containing an effective amount of at least one compounds of formula I according to claim 1, together with a pharmaceutically acceptable, non-toxic carrier.

6. A pharmaceutical composition according to claim 5 in dosage unit form containing from 0.1 ppm to 0.1% by weight of the dosage unit of a compound of formula I.

7. A method for the treatment of inflammatory diseases or diseases characterized by abnormal cell differentiation or cell proliferation which comprises administering to a patient in need of such treatment an effective amount of a pharmaceutical composition according to claim 1.

* * * * *

UNITED STATES PATENT AND TRADEMARK OFFICE
CERTIFICATE OF CORRECTION

Page 1 of 2

PATENT NO. : 5,710,142
DATED : January 20, 1998
INVENTOR(S) : Martin J. Calverley, et al.

It is certified that error appears in the above-identified patent and that said Letters Patent is hereby corrected as shown below:

On the title page:

item [73], "Bovens" should read -- Lovens --;

Column 2, line 63, "rumour" should read -- tumour --;

Column 5, before line 45, change the formula to read:

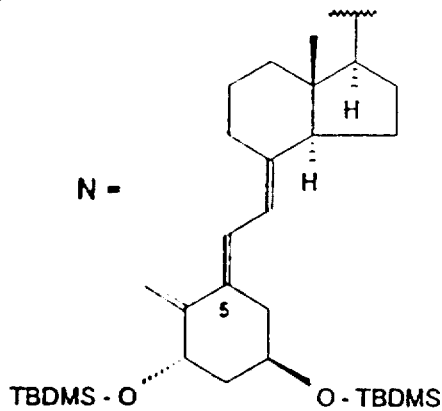

UNITED STATES PATENT AND TRADEMARK OFFICE
CERTIFICATE OF CORRECTION

PATENT NO. : 5,710,142
DATED : January 20, 1998
INVENTOR(S) : Martin J. Calverley, et al.

It is certified that error appears in the above-identified patent and that said Letters Patent is hereby corrected as shown below:

Column 7, line 28, after "preferable" insert -- to --;

Column 13, line 20, delete "H";

Column 17, line 45, "12H" should read -- 6H --;

Column 20, line 8, after "for" insert -- 90 --; and

Column 20, line 44, before "ethyl" insert -- 60% --.

Signed and Sealed this

Twenty-eighth Day of December, 1999

Q. TODD DICKINSON

Attest:

Attesting Officer

Acting Commissioner of Patents and Trademarks